United States Patent [19]

Adelman et al.

[11] Patent Number: 5,006,469

[45] Date of Patent: Apr. 9, 1991

[54] VECTORS AND HOST CELLS EXPRESSING PREPROMOTILIN AND MOTILIN-ASSOCIATED PEPTIDE (MAP)

[75] Inventors: John P. Adelman; Chris T. Bond; Gajanan Nilaver; Earl A. Zimmerman, all of Portland, Oreg.

[73] Assignee: Oregon Health Sciences University, Portland, Oreg.

[21] Appl. No.: 154,156

[22] Filed: Feb. 9, 1988

[51] Int. Cl.$^5$ .................. C12N 15/70; C12N 15/74; C12N 15/79; C12N 15/85

[52] U.S. Cl. .................. 435/240.1; 435/252.3; 435/252.31; 435/252.33; 435/320.1

[58] Field of Search .................. 435/68, 122.3, 235, 435/320, 240.1, 69.1, 252.3, 252.31, 252.33

[56] References Cited

U.S. PATENT DOCUMENTS 3,978,035 8/1986 Wunsch .................. 260/112.5 R

OTHER PUBLICATIONS

Brown, J. et al., Can. J. Biochem., 51, 533 (1973).
Schubert, H. et al., Can. J. Biochem., 52, 7 (1974).
Poitras, P. et al., Regulatory Peptides, 5 (1983), 197–208.
Suggs, S. V. et al., PNAS 78 (11) 6613–6617, 1981.
Brown, J. C. et al., Chem. Abstracts 79(5), 167, 1973.
Schubert, H. et al., Chem. Abstracts 80(23), 155, 1974.
Poitras, P. et al., Chem. Abstracts 98(2), #173375c, 1983.

Deg, D. et al., Oct. 1985, Am. J. Gastroenterology 80(10), 846.
Seino, Y. et al., 1987, FEBS Letters, 223/1, pp. 74–76.
Watson, J. D. et al., 1983 Recombinant DNA: a short course, W. H. Freeman & Co., pp. 86–89, 172–173,1–77–178,189–196 and 153.
Maniatis 1982, Molecular Cloning Cold Spring Harbor Laboratory, pp. 412–430.
Pearse et al., (1974), Virchows Arch. B Cell Path. 16:111–120.
Polak et al., (1975), Gut 16:225–229.
Polak et al., (1976), Scand. J. Gastroent. 11 (Suppl. 39):39–42.
Bond et al., Molecular Endocrinology (1988) 2(2):175–180.

Primary Examiner—Richard A. Schwartz
Attorney, Agent, or Firm—Irell & Manella

[57] ABSTRACT cDNA encoding a precursor peptide for motilin has been retrieved from porcine gut tissue. The precursor protein contains a motilin-associated peptide (MAP) sequence conjugated to the motilin peptide through a trypsin-like cleavage site. The MAP is useful in regulating alimentary physiology in vertebrates. The DNA provides a means to obtain the corresponding DNAs in other vertebrate species, including humans. It also makes available recombinant motilin, motilin precursor, and MAP of any desired species.

4 Claims, 2 Drawing Sheets

FIG. 2A

CANINE

INTESTINAL MOTILIN

Phe Val Pro Ile Phe Thr [His] [Ser] Glu Leu Gln [Lys] [Ile] [Arg] Glu Lys Arg Asn Lys Gly Gln $CA_C^T$ $\begin{matrix}TCX\\AGT_C\end{matrix}$ $AA_G^A$ $\begin{matrix}T\\ATC\\A\end{matrix}$ $\begin{matrix}AGA\\CGX\end{matrix}_G$

PORCINE

Phe Val Pro Ile Phe Thr [Tyr] [Gly] Glu Leu Gln [Arg] [Met] [Gln] Glu Lys Arg Asn Lys Gly Gln $TT_C^T$ GTX CCX $AT T_C^A$ $TT_C^T$ ACX $TA_C^T$ GGX $GA_G^A$ $\begin{matrix}CTX\\A\\TTG\end{matrix}$ $CA_G^A$ $\begin{matrix}AGA\\CGX\end{matrix}_G$ ATG $CA_G^A$ $GA_G^A$ $AA_G^A$ $\begin{matrix}AGA\\CGX\end{matrix}_G$ $AA_C^T$ $AA_G^A$ GGX $CA_G^A$

3' $GT_T^C$ $TC_C^T$ TAC $GT_C^T$ $CT_C^T$ $TT_C^T$ CT 5'

MOTILIN OLIGOS
32/20mers

FIG. 2B

MOTILIN

Lys Lys Glu Gly Lys Asn Arg Glu Lys Glu Gln Met Arg Gln Leu Glu Gly Tyr Thr Phe Ile Pro Val Phe Ala Glu

VECTORS AND HOST CELLS EXPRESSING PREPROMOTILIN AND MOTILIN-ASSOCIATED PEPTIDE (MAP)

TECHNICAL FIELD

The invention relates to recombinant production of proteins associated with feeding and digestion in vertebrates. More particularly, it concerns the peptide motilin and associated proteins involved in alimentation.

BACKGROUND ART

The 22 amino acid peptide, motilin, was isolated from porcine gut in 1971, and the amino acid sequence was determined. Analogous proteins having a high degree of homology have been isolated from the- gut of other species, including canine and rabbit. Present evidence indicates that motilin acts on the cholinergic neurons of the enteric plexis, and is associated with cyclic motor activity of the intestine.

Other tissues besides the gut have been assayed for the presence of motilin by immunoreaction using antisera prepared using immunization against natural porcine motilin, portions of the amino terminal and carboxy terminal portions of motilin, and a synthetic (14-Met) motilin. These assays gave conflicting results depending on the antisera chosen. One or another of these antisera reacts with a protein found in stomach, gall bladder, adrenals, salivary glands, cerebrospinal fluid, cerebral cortex, brain stem, hypothalamus, medulla, pituitary, pineal glands, and fibers of various sympathetic nerves. The inconsistent results obtained using various antisera has been considered by some to be evidence that motilin exists in different molecular weight forms (Pearse, A.G.E , et al, *Virchows Archive Cell Pathol* (1974) 16:111–120; Polak, J. M., et al, *Gut* (1975) 16:225–229; Polak, J. M., et al, *Scand J Gastroent* (1976) 11 (Suppl 39):39–42).

While it has been established that motilin plays an important role in the nutrition of vertebrates, its tissue of origin and control of its production have not been established. Accordingly, coordination of motilin levels in appropriate tissues with desired responses has not been possible. It has now been shown, using recombinant technology, that this peptide originates in the intestine. More important, it has now been shown that an unpredicted additional peptide, motilin-associated peptide (MAP), is encoded contiguous with the codons for motilin. MAP thus provides an additional tool for manipulation of the psychology and physiology of alimentation.

DISCLOSURE OF THE INVENTION

The invention provides recombinant materials and methods for the production not only of the known peptide motilin, but also of the previously unknown and unsuspected vertebrate motilin-associated peptide (MAP). The complete amino acid sequence of porcine MAP has been determined, and the cDNA encoding it has been retrieved. Thus, the invention supplies an additional peptide which is useful in the regulation of food consumption and usage by vertebrates, especially mammals.

Thus, in one aspect, the invention is directed to vertebrate, especially mammalian, MAP and to methods for its production and use. In another aspect, the invention is directed to DNA encoding prepromotilin or encoding motilin or MAP alone or with presequences, or encoding "motilin precursor", and to methods and materials for production of these peptides. In still another aspect, the invention is directed to a method to design DNA probes which comprises assuming maximal coding conservation in genes encoding peptides of various species.

BRIEF DESCRIPTION OF THE DRAWINGS

FIG. 2 shows a comparison of the canine and porcine motilin amino acid sequence and the design of oligonucleotide probes based on these peptides.

MODES FOR CARRYING OUT THE INVENTION

Figure 1:
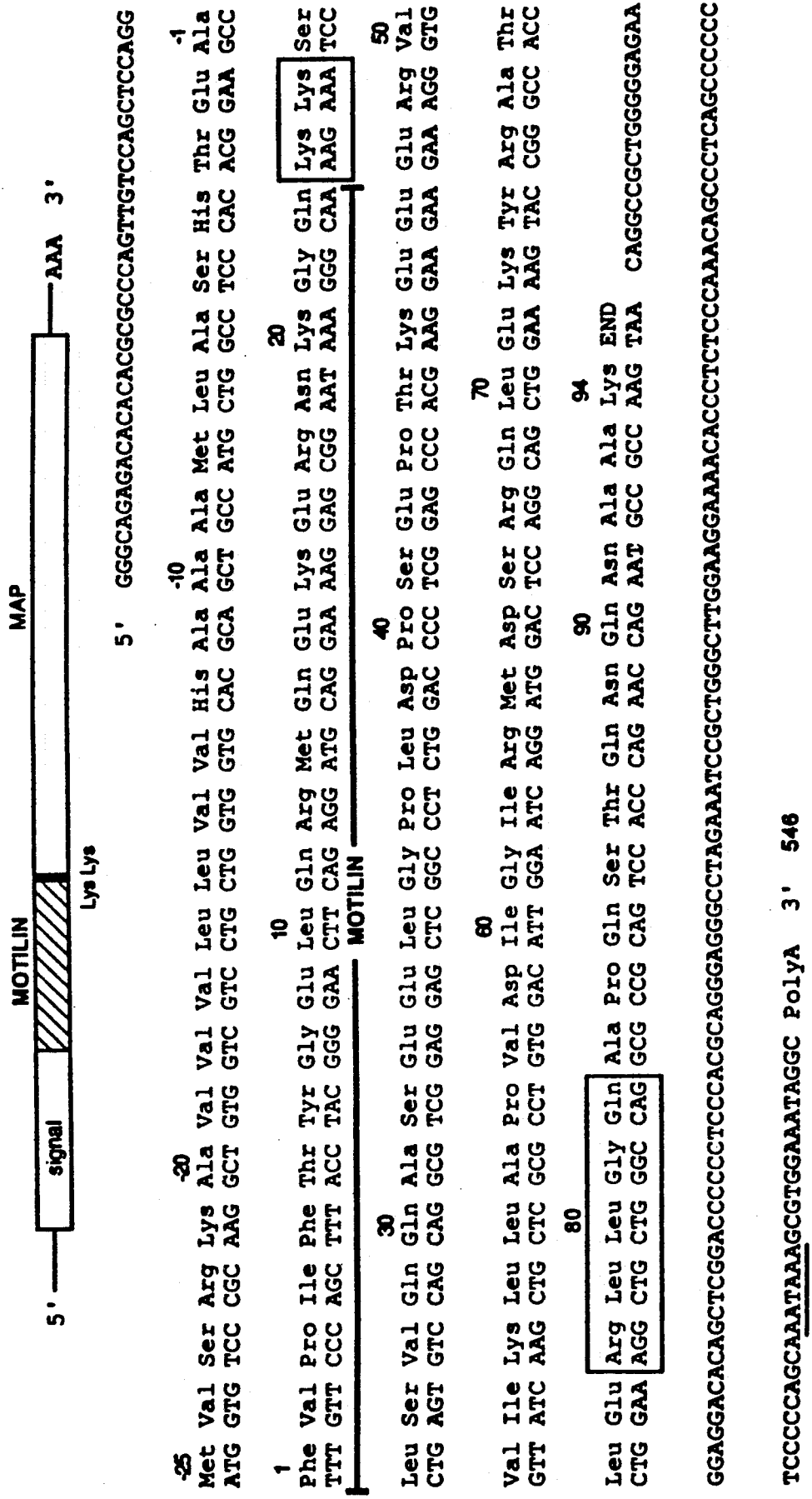
FIG. 1 shows the nucleotide and deduced amino acid sequence of porcine prepromotilin including the signal sequence, motilin itself, and MAP.

As used herein, "motilin-associated peptide" or "MAP" denotes a peptide of vertebrate, especially mammalian, origin encoded by prepromotilin RNA as a C-terminal peptide extension of motilin. A typical MAP is illustrated by the 70 amino acid peptide encoded by the sequence encoding residues 25–94 shown in FIG. 1 herein for the porcine prepromotilin sequence. Homologous sequences having at least 60%, and preferably 75% amino acid sequence homology, or when derived from more closely related species, at least 90% amino acid sequence homology to the porcine MAP sequence as found in other vertebrate species, and in the allelic variations and mutations thereof are included in the definition of vertebrate MAP. It is, of course, understood that the peptides may be in their neutral or acid-addition salt or basic salt forms, depending on the pH of their surroundings, as well as their derivatized forms, for example the acetylated or glycosylated forms. In addition, conservative amino acid substitutions, deletions, or additions—i.e., those which do not change the physiological activity of the MAP are also included within the definition.

"Motilin" is used in its usual sense to indicate the approximately 22 amino acid peptide found in various species exemplified by that indicated as residues 1–22 in FIG. 1 herein for the porcine sequence. Like MAP, motilin shows species variations, and allelic and mutational variants. Most species variations show at least 75% homology, or, if closely related, 90% homology.

"Motilin precursor" refers to a peptide which contains motilin linked through a cleavage site-to a motilin-associated peptide. This is also designated "promotilin" herein. This is exemplified and illustrated by the motilin precursor shown as residues 1–94 in FIG. 1. In this peptide, the motilin peptide is conjugated to the MAP through a trypsin-like cleavage site, Lys-Lys.

"Pre" in the name of a peptide, such as "pre"motilin, "pre"-MAP or "pre"promotilin, indicates the presence of a signal sequence upstream of the named peptide. Genes encoding these "pre"proteins are used for expression when secretion of the protein produced is desired.

"Expression vector" for a particular protein indicates a DNA sequence wherein the DNA encoding the desired protein is operably linked to control sequences capable of effecting its expression when the expression system is transformed, transfected, or otherwise inserted into a suitable host. Necessary elements of control sequences include suitable promoters, and putatively optional features of control sequences include other elements such as enhancers, terminating sequences, and so forth.

The illustrative porcine prepromotilin encoding DNA and the deduced amino acid sequence are shown in FIG. 2. As indicated in the figure, the DNA encoding residues −25 to −1 represents codons for a typical signal sequence with a hydrophobic region in its center and ended by an alanine residue. The sequence represented by residues 1-22 encodes the known amino acid sequence of porcine motilin. This is followed by codons for 2 lysine residues which provide a known cleavage site for trypsin-like enzymes. Trypsin-like enzymes cleave at the carboxy terminus of a lysine or arginine residues. The sequence encoding residues 25-94 encodes the 70 amino acid MAP. This protein was previously not known to exist. However, the indicated pentapeptide boxed at residues 78-82 represents a sequence homologous to corresponding pentapeptide sequence in PHI-27, a 27 amino acid peptide derived, along with vasointestinal peptide (VIP) from a common precursor. Along with gastric inhibitory peptide, all of these are members of the glucagon-secretin family.

The DNA sequence encoding porcine prepromotilin and its components provides at least three major benefits: the discovery of the previously unknown MAP, the ability to produce the physiologically active peptide segments recombinantly, and, especially in combination with the disclosure of the tissue of origin of motilin herein, the ability to obtain DNA sequences encoding the corresponding peptides from other vertebrate or mammalian species.

The newly discovered MAP is an important member of the glucagon-secretin family which regulates the physiology and psychology of alimentation. Accordingly, MAP, as well as motilin, has therapeutic value in regulating digestion, appetite, and nutrient absorption. The peptide can be, thus, administered to a subject in need of such systemic regulation in the form of pharmaceutical compositions suitable for administration of peptides or proteins, including injection by intravenous, intramuscular or intraperitoneal formulations, or by transmucosal or transmembrane administration, such as through nasal absorption. Oral formulations can also be used. Suitable compositions for injection include various excipients such as buffers and saline solutions, for example, Hank's solution, Ringer's solution and the like. Formulations for administration across membranes include various penetrants such as bile salts. The peptide is administered in an amount effective to elicit the desired effect on the physiology of the subject.

The DNA encoding MAP, motilin, motilin precursor, or the corresponding peptides provided with a signal sequence, such as prepromotilin (i.e., the complete coding sequence shown in FIG. 1) can be ligated into suitable expression vectors for recombinant protein production. Methods for effecting expression of DNA sequences encoding these desired proteins can be chosen from a variety of candidates. As the DNA provided contains no introns, procaryotic systems can be used; such systems include those appropriate for expression in E. coli, B. subtilis, and other bacterial systems. Typical promoters for use in these systems include the regulatable trp promoter and various modifications thereof. Also commonly used in procaryotic systems are phage promoters such as the $P_L$ promoter derived from λ phage. Expression systems in procaryotes include sequences transcribable into a ribosome binding site and suitable terminating sequences.

Eucaryotic microbes such as yeast and fungi can also be used. A wide variety of expression vectors which are adaptable to yeast are also known; suitable yeast promoters include those associated with the enzymes of the glycolytic pathway. For use in yeast and other eucaryotic systems, the coding sequence can also be provided derived directly from genomic DNA including any introns.

The DNA can also be expressed in tissue culture using cells derived from higher organisms such as mammalian or insect cells.

Suitable mammalian promoters include early and late promoters of SV40 virus (Fiers et al, Nature (1978) 273:113) or other viral promoters such as those derived from polyoma, adenovirus, bovine papilloma virus, or avian sarcoma viruses. Another promoter that can be used in mammalian cells is the metalothionine promoter. See, e.g., Uhler et al, J Biol Chem (1987) 262:15202-15207. Plant cells can be used as well, using, for example, the nopaline synthetase promoter (Depicker, A., et al, J Mol Apol Gen (1982) 1:561.

Techniques for construction of expression systems, construction of vectors for transferring the systems into the desired host, and methods for this transfer are known in the art. Typically, the desired coding DNA is ligated into operable linkage with the DNA sequences which provide the elements of the control sequence, and the expression package is ligated, either as a package or piecemeal into a suitable vector such as a plasmid or virus. The vector is then transferred into the host using methods known per se. In some instances, depending on the nature of the vector and the host, the vector replicates independently and is carried extrachromosomally as the cells divide; in other cases the vector is integrated into the host genome. The transformed cells containing the expression system are then grown under culture conditions suitable for the cells chosen. Advantageously, control sequences that can be regulated so as to be "turned on" only as desired are used to permit the transformed cells to multiply before the necessity to produce the foreign protein. Inducible promoters for various systems are known, including the trp promoter (induced by low tryptophan levels) and the $P_L$-promoter (induced by temperature changes) in procaryotes and the metallothionein promoter (induced by heavy metals) in mammalian systems.

The protein produced by the recombinant host is then harvested and recovered using means appropriate to the form in which the protein is made. If a presequence is included in a cell capable of processing it, the protein will be secreted into the medium or supernatant, and can be readily recovered after removing the cells, for example, by centrifugation, using appropriate purification techniques to isolate the protein from other proteins which may also be present in the medium. If no signal sequence is included, the protein will be produced intracellularly and must be recovered by lysing the cells and removing the cellular debris. The various proteins can also be produced as fusions with heterologous sequences; in these cases the heterologous portion of the sequence may desirably be removed using suitable cleavage sites which can advantageously be included in the construction of the encoding DNA.

In short, a wide variety of approaches to providing recombinantly produced motilin, MAP, or motilin precursor (promotilin) can be employed to provide these proteins.

The recombinant production of MAP or motilin precursor protein and the motilin peptides of certain species, in particular, human, provides these peptides in forms previously not available as the recombinant proteins are free of proteins normally accompanying them when in their native environment.

In addition to their production by recombinant techniques, motilin, MAP, and motilin precursor can also be synthesized using standard solid phase or liquid phase synthesis techniques for peptides. These techniques are known in the art per se. Solid phase synthesis of the peptides can be effected using commercially available instrumentation.

The availability of porcine cDNA encoding the precursor makes possible for the first time, the retrieval of DNA encoding the corresponding peptides in other species. While evolutionary drift is expected, the homology between various vertebrate species in the DNA encoding these peptides is high. Homology of about 80% is expected, and often 95% homology is found in closely related species. The availability of a DNA sequence of prepromotilin length assures the retrieval of the corresponding cDNA or genomic DNA from other vertebrate mammalian species such as human, canine, rabbit, bovine, feline, and so forth, as well as other vertebrate species such as avian species and fish such as salmon.

In addition to providing the suitable probe to obtain the sequences from the genome, the invention facilitates the retrieval of the corresponding cDNA by providing information as to the appropriate tissue source. It has been shown herein that the mRNA encoding the prepromotilin precursor, which includes the MAP encoding sequences is found in the intestinal tissue of pigs; and not in other tissues. Although a variety of tissues have been shown to be immunoreactive with various antisera prepared against motilin, as described in the Background section hereinabove, when these tissues were assayed by Northern blot, this analysis showed that the mRNA encoding prepromotilin resides exclusively in intestinal tissue. Thus, the invention provides not only the appropriate probe, but also the tissue from which the cDNA library should be made. The information as to source tissue and disclosure of the DNA sequence thus makes available the DNA encoding forms of motilin and MAP characteristic of other vertebrate species.

By providing the means to retrieve the cDNA encoding the corresponding proteins of other sequences, the invention makes available, for the first time, human motilin. This peptide has not hitherto been isolated. This protein is thus provided, for the first time, for therapeutic use.

Statement of Utility

The DNA of the invention provides the means for recombinant production of motilin, MAP, or motilin precursor, as well as the possibility for genetic manipulation of these peptides to alter their sequences toward an improvement of function or handling characteristics. In addition, the newly discovered MAP provides not only a tool for study of the interrelationships of proteins regulating alimentation, but also a therapeutic compound which can be used to effect such regulation in human and animal subjects.

EXAMPLES

The following examples are intended to illustrate but not to limit the invention.

EXAMPLE 1

Design of Oligonucleotide Probes

A preliminary attempt to obtain cDNA encoding porcine motilin by screening a cDNA library in λgt11 using antibodies prepared against this peptide was unsuccessful. Therefore, probes were designed for screening a cDNA library. The 22 amino acid sequence of porcine motilin, shown in FIG. 1, did not show regions which permitted the design of oligonucleotide pools of sufficiently limited numbers. Comparison of the porcine and canine motilin sequences, as shown in FIG. 2, provided a mechanism to minimize the number of oligonucleotides in the pool. The conservative difference between Lys12 (AAA/G) of the canine sequence and Arg12 (AGA/G, CGX) of the porcine sequence could be used to eliminate four possible choices for coding at Arg12 by assuming conservation of the coding sequences between these species; the Arg12 codon was assumed to be AGA/G. The oligonucleotides of the pool used to probe the cDNA library span amino acids GLn[11]–Glu[17] and are shown in FIG. 2.

EXAMPLE 2

Retrieval of Porcine Prepromotilin cDNA

Porcine intestinal mucosa was dissected by immediate removal of a length of duodenum following sacrifice. The tissue was cut longitudinally along the mesenteric border, the lumenal contents gently scraped away, and the mucosal layer of cells was teased away form the underlying muscular layers. Messenger RNA was isolated from the mucosa by the guanidine isothiocyanate/CsCl method described by Chirgwin, J. M., et al, *Biochemistry* (1979) 18:5294–5299, after the mucosa had been snap-frozen on dry ice. The poly-A+ fraction of the isolated RNA was selected by oligo-dT affinity purification, and 5 μg of the resulting mRNA was used to construct a cDNA library by the method of Geubler, U., et al, *Gene* (1983) 25:263–269, to obtain $2 \times 10^6$ independent recombinant λ phage.

In this method, the cDNA was ligated to EcoRI adapters and size selected for more than 400 bp by polyacrylamide gel electrophoresis; the eluted cDNA was then ligated to EcoRI-digested λgt10 DNA, in vitro packaged, and the phage used to infect *E. coli* C600hfl cells (Huynh, T., et al, in "DNA Cloning: A Practical Approach" (1984) D. Glover (ed) IRL, Oxford).

About $2 \times 10^5$ of the phage were screened using plaque hybridization. The recombinant phage-infected *E. coli* cells were plated to yield approximately 30,000 phage per 15 cm plate. Duplicate filters were prepared from each plate and incubated with oligonucleotide radiolabeled to a specific activity of $5 \times 10^6$ cpm/mole by incubation with γ-$^{32}$P ATP and polynucleotide kinase. Incubation was at room temperature for the oligonucleotide probes.

Following more than 16 hr incubation with oligonucleotide probes, filters were washed in 3 M trimethylammoniumchloride (TMACl) at 55° C. as described by Wood, W. I., et al, *Proc Natl Acad Sci (USA)* (1985) 82:1585–1588). Phage which were positively hybridizing in duplicate were plaque purified by repeated screening at reduced densities.

The recombinant phage DNA was prepared as described by Huynh, T. (supra) and the cDNA inserts were subcloned into phage M13 to provide a template for primed dideoxy chain termination sequence reactions as described by Sanger, F., et al, *Proc Natl Acad Sci (USA)* (1977) 74:5463–5467, or Messing, J., et al, Nucleic Acids Research (1981) 9:309–321).

EXAMPLE 3

Results of DNA Sequencing

The retrieved porcine cDNA insert showed an open reading frame encoding for a 119 amino acid peptide (13 kd) with the characteristics of a polyfunctional protein precursor, as shown in FIG. 1. The signal sequence shown as residues −25 to −1 is initiated by an ATG start codon and is preceded by nucleotides showing homology to canonical sequences for translation initiation in mammalian systems. The typical signal sequence shown as −25 to −1 in the figure is followed by a 22 amino acid sequence corresponding to the known sequence for porcine motilin followed by a Lys-Lys trypsin cleavage site as found in many polyprotein precursors; this is followed by the sequence encoding the new 70 amino acid peptide, MAP. This peptide is terminated by a stop codon followed by a 3' untranslated region which contains a polyadenylation signal and a poly-A+ tail.

EXAMPLE 4

Gene Homology and Tissue Distribution

The cDNA insert was used as a hybridization probe to screen additional independently derived clones. All of the additional cDNA clones encoded an identical protein and only a few conservative nucleotide substitutions, assumed to be polymorphisms, were exhibited.

Poly-A+ RNAs from brain and peripheral tissues were also screened with this probe. The mRNAs were fractionated on 1.4% agarose gels in 0.01 M phosphate after denaturing at 50° C. in 5 M glyoxal and were transferred to Nytran membranes as described by Melton, D. A., et al, *Nucleic Acids Research* (1984) 12:7035–7056.

Radiolabeled strand-specific riboprobes complementary to the motilin RNA were applied to the electrophoresed mRNA from rat pituitary cells, porcine pituitary, porcine adrenal gland, porcine duodenum, porcine cerebellum, porcine cortex, porcine hypothalmus, and porcine hypocanthus. Even when hybridized and washed at low stringency, no specific bands appear in lanes representing tissues other than that containing mRNA extracted from duodenum. A positive control blot probed for IB-15A mRNA known to be produced in virtually all tissues gave the expected bands. Thus, it appears that the precursor mRNA occurs only in gut tissue, among those surveyed.

We claim:

1. A recombinant expression vector comprising control sequences operably linked to a DNA encoding a protein functionally equivalent to motilin precursor or preprotein forms thereof, said DNA including a nucleotide sequence substantially equivalent to the sequence depicted in FIG. 1 encoding for amino acid residues 1–94.

2. A recombinant expression vector comprising control sequences operably linked to a DNA encoding a protein functionally equivalent to MAP or preprotein forms thereof, said DNA including a nucleotide sequence substantially equivalent to the sequence depicted in FIG. 1 encoding for amino acid residues 25–94.

3. A recombinant host cell transformed with the expression vector of claim 1.

4. A recombinant host cell transformed with the expression vector of claim 2.

* * * * *